(12) United States Patent
Bucay-Couto et al.

(10) Patent No.: US 7,906,125 B2
(45) Date of Patent: Mar. 15, 2011

(54) SOLID OR SEMI-SOLID THERAPEUTIC FORMULATIONS

(75) Inventors: Weenna Bucay-Couto, Burlington, MA (US); Sheng-Ping Zhong, Shrewsbury, MA (US); Arthur Madenjian, Winchester, MA (US); Enxin Ma, Natick, MA (US); Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1822 days.

(21) Appl. No.: 10/664,601

(22) Filed: Sep. 18, 2003

(65) Prior Publication Data

US 2005/0064008 A1   Mar. 24, 2005

(51) Int. Cl.
*A61K 9/00*   (2006.01)
*A01N 63/00*   (2006.01)

(52) U.S. Cl. .................... 424/400; 424/93.2
(58) Field of Classification Search ........... 604/70; 514/724; 600/458; 424/400
See application file for complete search history.

(56) References Cited

U.S. PATENT DOCUMENTS

| | | | |
|---|---|---|---|
| 4,927,806 A | 5/1990 | Kramer et al. | 514/2 |
| 5,147,631 A * | 9/1992 | Glajch et al. | 424/9 |
| 5,469,854 A * | 11/1995 | Unger et al. | 600/458 |
| 5,733,572 A * | 3/1998 | Unger et al. | 424/450 |
| 5,770,222 A * | 6/1998 | Unger et al. | 424/450 |
| 6,123,923 A * | 9/2000 | Unger et al. | 424/9.52 |
| 6,168,777 B1 | 1/2001 | Greff et al. | 424/1.25 |
| 6,228,398 B1 * | 5/2001 | Devane et al. | 424/484 |
| 6,231,591 B1 | 5/2001 | Desai | 606/210 |
| 6,277,391 B1 * | 8/2001 | Seo et al. | 424/426 |
| 6,443,898 B1 * | 9/2002 | Unger et al. | 600/458 |
| 6,461,296 B1 | 10/2002 | Desai | 600/210 |
| 6,495,164 B1 | 12/2002 | Ramstack et al. | 424/489 |
| 6,869,927 B1 * | 3/2005 | Gentz et al. | 514/2 |
| 6,905,475 B2 * | 6/2005 | Hauschild et al. | 604/70 |
| 7,015,253 B2 * | 3/2006 | Escandon et al. | 514/724 |
| 2002/0010150 A1 * | 1/2002 | Cortese et al. | 514/54 |
| 2002/0082610 A1 | 6/2002 | Cioanta et al. | 606/108 |
| 2003/0064998 A1 | 4/2003 | Francois et al. | 514/259.41 |
| 2003/0130575 A1 * | 7/2003 | Desai | 600/417 |
| 2005/0064046 A1 | 3/2005 | DiTrolio | 424/680 |

FOREIGN PATENT DOCUMENTS

| | | |
|---|---|---|
| EP | 1 078 636 A1 | 2/2001 |
| EP | 1 197 208 A1 | 4/2002 |
| GB | 811717 | 4/1959 |
| WO | WO 03/005889 A2 | 1/2003 |

OTHER PUBLICATIONS

Rehman, J.; Tissue Chemoablation,(2003),Journal of Endourology, vol. 17, No. 8: p. 1.*
Joseph V. Ditrolio, "A Novel Treatment for BPH: Transurethral Ethanol Ablation of the Prostate (TEAP)," slide presentation, 20th World Congress on Endourology & Shockwave, Sep. 20, 2002, Genoa, Italy, 3 pp.

* cited by examiner

*Primary Examiner* — Sreeni Padmanabhan
*Assistant Examiner* — Timothy E Betton
(74) *Attorney, Agent, or Firm* — Mayer & William PC; David B. Bonham; Keum J. Park

(57) ABSTRACT

An injectable or insertable dosage form comprising a biodisintegrable binder and an ablation agent in a concentration effective to cause tissue necrosis. The injectable dosage form is a solid or semi-solid dosage form. Due to the solid or semi-solid nature of the dosage form, retention at the site of injection or insertion is improved, thereby improving delivery efficiency of the ablation agents within the dosage form and/or reducing the nonspecific tissue damage associated with the dosage form.

24 Claims, 1 Drawing Sheet

SOLID OR SEMI-SOLID THERAPEUTIC FORMULATIONS

FIELD OF THE INVENTION

The present invention relates to formulations and methods for chemoablation of tissue, such as prostate tissue. More particularly, the present invention relates to solid or semi-solid formulations for direct injection or insertion into tissue (e.g., the prostate), leading to ablation of the tissue.

BACKGROUND OF THE INVENTION

Prostate diseases such as prostatitis, benign prostatic hypertrophy, prostatodynia, and prostate carcinoma afflict many adult males. The largest population of men stricken with prostate problems are those over age fifty. However, inherited prostate problems can appear in much younger men.

Benign prostatic hypertrophy is a condition where the prostate over-grows or becomes enlarged. Prostate growth is controlled by androgen receptors found in the prostate gland. When the androgen receptors are stimulated by 5-alpha-dihydrotesterone (DHT), they cause the prostate to grow. DHT is produced by an enzymatic conversion of testosterone in the prostate.

Over the past twenty years a variety of approaches have been developed to treat benign prostatic hypertrophy. In general, these approaches alter the prostatic tissue volume or the biochemistry of the prostate, and they include the application of heat, cold, chemical agents, pharmaceutical agents and radiation. In recent years, a number of minimally invasive technologies have been developed, including radiation, RF ablation, microwave ablation, cryogenic ablation/freezing, and chemo-ablation. Chemo-ablative approaches, including injection of alcohol or salt solutions, have been evaluated for the treatment of benign prostatic hypertrophy. However, the lack of delivery control when administering presently known ablative liquids has led to unpredictable retention of the same, leading to nonspecific ablation of both the prostate as well as surrounding tissues and organs.

SUMMARY OF THE INVENTION

The above and other needs and challenges are addressed by the present invention.

According to an aspect of the present invention, injectable or insertable dosage forms are provided, which comprise a biodisintegrable binder (e.g., a biodisintegrable polymer or organic compound) and a chemical ablation agent (e.g., a salt) in an amount effective to cause tissue necrosis, wherein the injectable or insertable dosage forms are solid or semi-solid dosage forms. In various embodiments, the dosage forms comprise an optional contrast agent in an amount sufficient to render the dosage forms visible using noninvasive monitoring techniques and/or optional additional therapeutic agents.

Other aspects of the present invention are directed to methods of treating prostatic tissue diseases or conditions, such as benign prostatic hypertrophy, comprising injecting or inserting a prostatic dosage form like those above into the prostate of a patient.

In other aspects of the present invention, injectable or insertable dosage forms like those above are used in the treatment of tissue, including prostatic tissue, kidney tissue, liver tissue, bladder tissue, benign tumors and malignant tumors.

Still other aspects of the present invention are directed to methods of forming dosage forms like those above, for example, using solvent-based techniques, melt techniques and/or dispersion/emulsion stabilization techniques.

One advantage of the present invention is that injectable or insertable formulations are provided, which display improved retention of ablative agents in tissue such as prostatic tissue, thereby improving delivery efficiency while minimizing adverse effects such as nonspecific damage.

Another advantage of the present invention is that injectable or insertable formulations are provided, which are capable of being detected by noninvasive monitoring techniques, including ultrasound, X-ray fluoroscopy and magnetic resonance imaging (MRI). In this way, the quantity and location of the injectable or insertable formulations can be more precisely monitored and controlled.

These and other embodiments and advantages of the present invention will become immediately apparent to those of ordinary skill in the art upon review of the Detailed Description and Claims to follow.

DETAILED DESCRIPTION OF THE INVENTION

Figure 1:
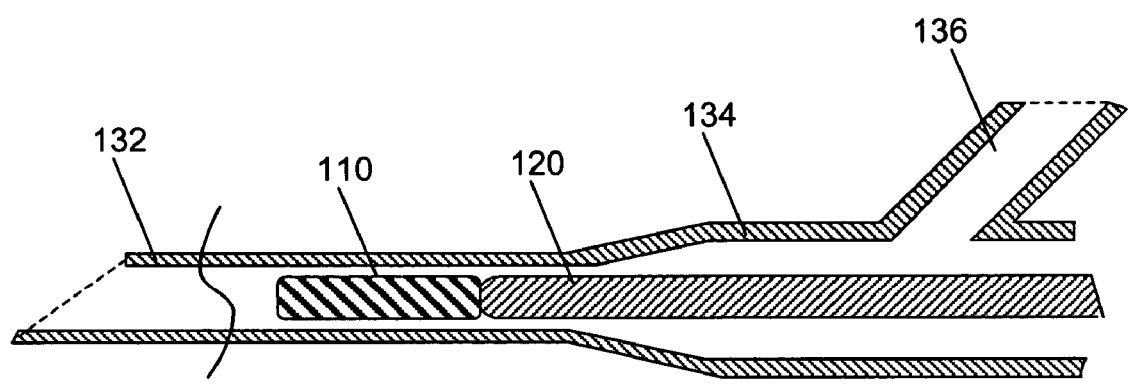
FIG. 1 is a schematic partial cross-sectional view of one embodiment of a device for delivery of a dosage form in accordance with the present invention.

According to an aspect of the present invention, injectable or insertable dosage forms are provided, which comprise a biodisintegrable binder and a chemical ablation agent in an amount effective to produce necrosis in the tissue that is exposed to the dosage form. The dosage forms are solid or semi-solid materials, which result, for example, in improved dosage retention in the tissue (e.g., there is little to no back-leakage into the injection tract), thereby improving delivery efficiency of the ablation agents and/or minimizing the adverse effects such as nonspecific tissue damage.

As defined herein, a "solid or semi-solid" material is a material having a distinct shape (e.g., spherical, rod-shaped, cubic, etc.), which is substantially retained prior to and during insertion, although the dosage form may deform somewhat during handling. Chemical ablation agents are materials whose inclusion in the solid or semi-solid dosage forms of the present invention in effective amounts results in necrosis (death) or shrinkage of nearby tissue upon injection or insertion of the formulation into the tissue. A wide range of ablation agent concentrations are utilized in the formulations of the present invention, with the amounts employed varying, depending on the characteristics of the ablation agent, the tissue, and the biodisintegrable binder (discussed below), among other factors. Typical concentration ranges are from about 1 to 95 wt % of ablation agent, more typically about 5 to 80 wt %.

In some embodiments, the ablation agents are osmotic-stress-generating agents, for example, a salt, such as sodium chloride or potassium chloride. The process of osmosis is the passage of at least one diffusible species (commonly, water) through a semi-permeable membrane (e.g., the membranes that surround all cells in the body), which membrane simultaneously prevents the passage of at least one non-diffusible species (e.g., salt). In osmosis, the passage of the diffusible species is from a less concentrated solution (with respect to the non-diffusible species) through the membrane to a more concentrated one. What determines the relative concentration of the diffusible species is the amount of non-diffusible species present on either side of the membrane. Osmotic pressure is generated whenever environments of different water concentration are separated by a semi-permeable membrane, and will remain until the two solutions are of equal concentration. This is why cells frequently swell (and even burst, in some cases), when placed in distilled water, and why they frequently shrivel when placed in aqueous solutions containing high concentrations of a non-diffusible agent, such as salt (or when exposed to pure salt). If cells are subjected to sufficient osmotic stress, they will die.

In other embodiments, the ablation agents are basic agents such as sodium hydroxide, acidic agents such as acetic acid and formic acid, and/or enzymes such as collagenase, hyaluronidase, pronase, and papain.

In other embodiments, the ablation agents are free-radical generating agents, for example, hydrogen peroxide, potassium peroxide or other agents that can form free radicals in tissue, such as prostate tissue. Upon formation, the free radicals will attack the tissue to create necrosis. For example, free radicals can be formed by decomposition of the free-radical generating agent upon exposure to water, exposure to heat, exposure to light and/or exposure to other agents.

In still other embodiments, oxidizing agents, such as sodium hypochlorite, hydrogen peroxide or potassium peroxide, tissue fixing agents, such as formaldehyde, acetaldehyde or glutaraldehyde, or naturally occurring coagulants, such as gengpin, are used as ablation agents.

The biodisintegrable binder is generally provided within the dosage form in an amount effective to provide the dosage form with suitable solid or semi-solid characteristics. Hence, a wide range of biodisintegrable binder concentrations are utilized in the formulations of the present invention, with amounts varying based on the characteristics of both the ablation agent and the biodisintegrable binder, among other considerations. Typical ranges are from about 1 to 80 wt % of biodisintegrable binder, more typically about 5 to 50 wt %.

A "biodisintegrable" binder is a binder that, once injected or inserted into tissue such as the prostate, undergoes dissolution, degradation, resorption and/or other disintegration processes. Due to the inclusion of such binders, dosage forms in accordance with the present invention will typically undergo at least a 10% reduction in weight after residing in tissue such as prostate tissue for a period of 7 days, more typically a 50-100% reduction in weight after residing in the tissue for a period of 4 days.

Biodisintegrable binders for use in connection with the present invention include biodisintegrable compounds such as glycerine, and biodisintegrable polymers. As the term is used herein, a polymer can consist of as few as two monomeric units. The biodisintegrable polymers for use in conjunction with the present invention can be of natural or synthetic origin, can be homopolymers or copolymers, and can be selected, for example, from the following: cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CM-HEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(ε-caprolactone-co-glycolide), carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide and poly(ethylene oxide-propylene oxide) (e.g., Pluronic acid from BASF), polyoxyethylene (polyethylene glycol), polyanhydrides, polyvinylalchol, polyethyleneamine and polypyrridine, additional salts and copolymers beyond those specifically set forth above, and blends of the forgoing (including mixtures of polymers containing the same monomers, but having different molecular weights).

The formulations of the present invention also optionally comprise therapeutic agents in addition to the ablation agents described above. "Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, and (r) hormones.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

A wide range of therapeutic agent loadings can be used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

The prostate injection formulations of the present invention also optionally include one or more imaging contrast agents, in addition to the ablation agents, biodisintegrable binders, and optional therapeutic agents discussed above. The ability to non-invasively image the body regions where the formulations of the present invention have been introduced (and by default where they have not been introduced) is a valuable diagnostic tool for the practice of the present invention. Among such currently available non-invasive imaging techniques are included magnetic resonance imaging (MRI), ultrasonic imaging, x-ray fluoroscopy, nuclear medicine, and others. Various categories of imaging technology have associated with them imaging contrast agents, i.e., substances that enhance the image produced by medical diagnostic equipment.

For example, x-ray based fluoroscopy is a diagnostic imaging technique that allows real-time patient monitoring of motion within a patient. To be fluoroscopically visible, formulations are typically rendered more absorptive of x-rays than the surrounding tissue. In various embodiments of the invention, this is accomplished by the use of contrast agents. Examples of contrast agents for use in connection with x-ray fluoroscopy include metals, metal salts and oxides (particularly bismuth salts and oxides), and iodinated compounds. Examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine.

Ultrasound and magnetic resonance imaging can provide two-and/or three-dimensional images of a portion of the body. Ultrasound and MRI are advantageous, inter alia, because they do not expose the patient or medical practitioner to harmful radiation and can provide detailed images of the observed area. These detailed images are valuable diagnostic aids to medical practitioners and can be used to more precisely control the quantity and location of the formulations of the present invention.

Magnetic resonance imaging (MRI) produces images by differentiating detectable magnetic species in the portion of the body being imaged. In the case of $^1$H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and, thereby, allow for enhanced contrast and better images of the area of interest. For contrast-enhanced NMRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest. Paramagnetic ion chelates can be, for example, attached to the biodisintegrable binder or they can simply be admixed with the other components of the formulation. Further information can be found, for example, in U.S. patent application No. 20030100830 entitled "Implantable or insertable medical devices visible under magnetic resonance imaging," the disclosure of which is incorporated herein by reference.

Ultrasound uses high frequency sound waves to create an image of living tissue. A sound signal is sent out, and the reflected ultrasonic energy, or "echoes," used to create the image. Ultrasound imaging contrast agents are materials that enhance the image produced by ultrasound equipment. Ultrasonic imaging contrast agents introduced into the formulations of the present invention can be, for example, echogenic (i.e., materials that result in an increase in the reflected ultrasonic energy upon injection or insertion of the formulation) or echolucent (i.e., materials that result in a decrease in the reflected ultrasonic energy upon injection or insertion of the formulation).

Suitable ultrasonic imaging contrast agents for use in connection with the present invention include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid). Microbubbles can also be used as ultrasonic imaging contrast agents as is known in the imaging art. The ultrasonic imaging contrast agents for use in connection with the present invention are preferably biocompatible and stable in the formulation. Concentrations of the ultrasonic imaging contrast agents typically range from about 0.01 wt % to 10 wt % of the formulation, more typically about 0.05 to 2 wt %, where solid particles are used.

Because they are solid or semisolid in consistency, the dosage forms of the present invention can be provided in an essentially unlimited variety of shapes (e.g., spheres, cylinders, irregular shapes including beads of various shapes) and sizes, ranging from microparticles to pellets (e.g., having largest dimensions ranging from 1 micron to 3 microns to 10 microns to 30 microns to 100 microns to 300 microns to 1 mm to 3 mm to 30 mm and all ranges in between). For example, where pellets are utilized, they typically have a largest dimensions ranging from 1 to 30 mm, more typically from 3 to 10 mm. As a more specific example, cylindrical pellets can be provided, which have an outside diameter ranging from 1 to 3 mm and a length ranging from 3 to 10 mm. The formulations can be matrix formulations (e.g., matrix microspheres), encapsulated formulations (e.g., encapsulated microspheres), and so forth.

In many embodiments, the dosage forms of the present invention are coated, for example, to protect the dosage forms, or to delay delivery of the ablation agent (e.g., until the dosage forms are properly positioned). The dosage forms can be fully coated or partially coated. For instance, it may be desirable to coat only the forward (relative to the direction of insertion) or rearward portions of the dosage forms. Beneficial polymers for coating the dosage forms include biodisintegrable polymers such as those discussed above.

Subjects for the procedures of the present invention include vertebrate subjects, typically mammalian subjects, more typically human subjects. The formulations of the present invention are injected/inserted into tissue by a variety of routes and using a variety of apparatuses.

Examples of tissue for treatment in accordance with the present invention include prostatic tissue, kidney tissue, liver tissue, bladder tissue, or any other organ or entity confined by a capsular membrane. The treated tissue may comprise benign tumor tissue or malignant tumor tissue. For example, disease states for which the treatment may be useful include, BPH, prostate cancer, prostitis, any other disease states occurring within a capsular membrane-confined organ. The solid salt dosage forms are inserted by any of a variety of routes, including transabdominal, transperineal, transcutaneous, transurethral, and transrectal routes of insertion. Other routes may be suitable depending on the application and location of tissue, which ensures access through the capsular membrane. Where prostatic tissue is to be treated, transperineal, transurethral, and transrectal routes are typically used, with transrectal administration being particularly beneficial.

Where discrete dosage forms (e.g., pellets, as opposed to a powder) are utilized, between 1 and 10 dosage forms are commonly injected or inserted per site. This number may vary, depending on different parameters, for example, the configuration and makeup of the pellet, the tissue being treated, the size of desired treatment zone, and so forth. Where prostatic tissue is treated, from 3 to 10 pellets are commonly inserted into each lobe of the prostate.

Because the dosage forms of the present invention are in solid or semi-solid form, they can be injected/inserted in some embodiments by simply pushing (e.g., by mechanical, hydraulic or pneumatic action) the dosage forms through a cylinder (e.g., a 10 gauge or smaller needle) via a push rod or other means, without the need to form a fluid-tight seal between the push rod and the surrounding cylinder.

For example, FIG. 1 is a cross-sectional illustration of an apparatus, which comprises a body 134 and a needle 132. The body is further provided with a side port 136 through which a solid or semisolid dosage form (which may be deformable) is introduced. Subsequently, a sampler pusher 120 (e.g., a mandrel or modified obturator) is used to push the dosage form 110 into the barrel of the needle 132. If desired, an additional side port (not illustrated) can be employed for introduction of the sample pusher 120. Once the needle 132 is inserted to the desired position within the patient's tissue (not illustrated), the sampler pusher 120 is used to push the dosage form 110 from the needle 132 into the tissue, after which the needle 132 is withdrawn. In some instances it may be desirable to withdraw the needle by a short distance, allowing the dosage form to be pushed into an opening in the tissue created by the needle. In some embodiments, stoppers (not illustrated) are employed to control the depth to which the needle is inserted and/or the depth to which the sample pusher is inserted. As noted above, due to the solid or semi-solid nature of the dosage form, retention at the site of injection is improved (e.g., the dosage form does not flow), thereby improving delivery efficiency of the ablation agents within the dosage form and/or reducing nonspecific tissue damage associated with the dosage form.

In other even more straightforward embodiments the dosage form is injected/inserted using an apparatus consisting of a simple needle and sample pusher (e.g., a mandrel or modified obturator). For example, according to one embodiment, a dosage form (e.g., a rod-shaped dosage form or beads) is placed in the needle. Once the needle is inserted at the desired depth and location, the pusher is used to push the sample from the needle and into the tissue. In still other embodiments, the sample pusher is provided with a holding clip or it is provided with a hollow end to secure the sample up to the time of delivery.

In still other embodiments, the dosage form is injected/inserted via jet injection. Jet injection is a means of administering the dosage forms without the use of needles. Typically, a compression system (e.g., mechanical, or a gas such as helium, nitrogen, carbon dioxide, etc.) is used to accelerate the dosage forms to a relatively high velocity, allowing them to penetrate the tissue. Jet injector devices can be, for example, disposable, or reusable with medication cartridges that are prefilled or non-prefilled medication cartridges. Examples of jet injectors include Biojector® from Bioject, N.J., USA and the PowderJect® System from PowderJect, UK (designed to inject a dry powder formulation of microparticles, by accelerating them to high speed within a helium gas jet). In addition, such injection methods enable dispersion control (depth and width) of the injectate.

The dosage forms of the present invention can be formed by various techniques. For example, in embodiments where the biodisintegrable binder has thermoplastic characteristics, a melt can be formed which contains the ablation agent and biodisintegrable binder. In other instances, solutions or dispersions (including slurries and pastes) of the ablation agent and biodisintegrable binder are formed. In either case, the resulting fluid (i.e., the melt, solution or dispersion) can be processed into a desired solid or semi-solid shape.

For example, in some embodiments, the resulting fluid is poured into a mold and solidified (e.g., by cooling the melt, or by evaporating the solvent from the solution/dispersion). The resulting solidified mass is then used in its molded shape or it is processed further (e.g., by grinding, breaking, cutting, sculpting, etc.) to achieve a desired shape.

In other embodiments, the resulting fluid is extruded, molded, dripped, sprayed, etc., after which it is solidified, for example, by cooling the melt, by removing the solvent from the solution/dispersion (for instance, by evaporation into a heated gas or contact with another solvent), or by crosslinking the solution/dispersion, among other techniques. As above, the resulting mass is then used as is, or it is further processed to achieve a desired shape. Where extrusion is employed, it is possible to co-extrude one or more coating layers on an underlying extrudate.

As yet another example, the melt or solution/dispersion can be mixed with a larger volume of an immiscible solvent, whereupon sufficient shear is applied to disperse the melt or solution/dispersion within a continuous phase occupied by the immiscible solvent. The dispersed phase (occupied by the melt or solution/dispersion) is subsequently stabilized, for example, (a) by cooling the dispersed melt to form a solid dispersion, (b) by coating or crosslinking the outer surface of the dispersed solution/dispersion, or (c) by removing the solvent from the dispersed solution/dispersion. As above, the resulting beads or particles can then be used as produced, or they can be processed further to achieve a desired shape.

Once a dosage form of the desired shape is obtained, it may be subjected to further coating processes, for instance by dipping in or spraying with a polymer dispersion or solution, followed by crosslinking in some instances.

Prior to injection or insertion, the dosage forms of the present invention are typically sterilized, for example, by exposing them to heat, radiation or ethylene oxide gas, or by preparation under aseptic conditions.

The invention is further described with reference to the following non-limiting Examples.

EXAMPLE 1

5 g of carboxymethylcellulose 7HF PH (CMC, Blanose Type, Hercules Inc.) was dissolved in 100 ml of saturated sodium chloride solution (~26% w/w). The polymer is then extruded through an 18G needle into a 70% ethanol solution to form a rod/filament. The sodium chloride solution may be over-saturated, with the excessive sodium chloride particles suspended in the thick paste of CMC. The dried rod/filament is cut to desired length, typically 1 cm, for easy delivery.

EXAMPLE 2

The dosage forms produced in Example 1 are spray-coated with one or more layers of an aqueous solution of CMC (~1% w/w) to increase the strength of the dosage forms. The coated dosage forms are then air dried, or they are dehydrated in ethanol followed by air drying.

EXAMPLE 3

50 ml of CMC/sodium chloride solution from Example 1 and 50 ml of a 3 wt % sodium alginate (from Protanal, LF 10/60) aqueous solution are mixed thoroughly. The mixture is extruded into absolute ethanol bath to provide a solid rod. The rod is then crosslinked using a calcium chloride solution (e.g., at a concentration of 30 wt %) by dipping the rod into the $CaCl_2$ bath. Excess calcium chloride is removed by rinsing in ethanol.

EXAMPLE 4

The mixture from Example 3 is extruded into a 30 wt % calcium chloride bath, instead of absolute ethanol, to form a solid rod/filament. This filament/rod is then air dried and cut into 1 cm lengths for delivery.

EXAMPLE 5

The mixture from Example 3 is dispersed in a mineral oil or a silicone oil bath under agitation. Microbeads are formed in the bath. The size of the beads may be controlled by the speed of the agitation. 30 wt % calcium chloride solution is added into the bath to crosslink the alginate beads. The reaction is allowed to continue overnight to obtain solid beads. The beads are collected and washed in ethanol. After thorough drying, the beads are ready for delivery.

EXAMPLE 6

Sodium alginate is dissolved in water forming a first solution. CMC is dissolved in salt solution as above to form a second solution. The two solutions are co-extruded, with the inner extrudate (which emerges from the extrusion die in the shape of a rod) containing CMC and salt, and the outer extrudate (which emerges from the extrusion die in the shape of a tube) containing alginate and forming a crosslinkable coating around the inner extrudate. The coextruded product is dropped into a calcium chloride bath to crosslink the alginate in the coating. The crosslinked material is then dried. Washing the material in ethanol can accelerate the drying.

EXAMPLE 7

2 g of CMC powder and 8 g of sodium chloride powder are mixed thoroughly. About 8 g of water are added dropwise into the mixed powder with stirring. A uniform thick paste is formed. The paste is then extruded through the opening of a 5 ml syringe (Becton Dickinson Co.) to form a uniform filament/rod. The filament/rod is allowed to dry in the air at room temperature overnight. The dried filament/rod has an OD of about 1 mm. It is cut into 1 cm lengths in preparation for use.

EXAMPLE 8

The same mixing, extrusion and drying procedures as set forth in Example 7 are used with the following: 2 g dextran sulfate (from Bioworld), 8 g Sodium Chloride and 2 g water. A solid filament/rod is obtained and cut. The resulting rod has the following dimensions: OD=1 mm, length 1 cm.

EXAMPLE 9

A solution is formed that contains 10 wt % of poly(DL-lactide-co-glycolide (from Aldrich, lactide:glycolide, molar ratio=85:15) dissolved in THF. The rods from Examples 7 and 8 are coated with this solution. The rods are dipped into the solution three times to achieve the desired coating thickness. Alternatively, a spray coating technique may be used. The coating should be about 5 microns in thickness, and is allowed to dry in air at room or elevated (e.g., 50° C.) temperature. The dried coated rods are cut into 1 cm lengths for use (if not cut prior to coating).

EXAMPLE 10

An absorbable polymer, for example, PGA (poly-glycolic acid) is compounded with NaCl to form a matrix. This may be carried out, for example, using a Baybender compounding machine (or other compounder) to mix and blend the components. The resulting compounded mixture is then extruded or molded into various forms for implantation. The breakdown of the PGA within the body will expose and release the salt. Compounding is beneficial in that it potentially provides a greater polymer surface area for breakdown of the structure and absorption of the polymer. An added potential benefit of compounding the salt into the polymer is the delayed release of the salt (i.e., it can be dependent upon to polymer degradation). On the other hand, if the concentration of salt is high enough to create contiguous pockets within the matrix structure (i.e., producing a sponge-like structure), rapid breakdown of the polymer is expected to occur after the salt is gone.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An injectable or insertable dosage form for producing specific necrosis of tissue that comes into contact with the dosage form comprising: a biodisintegrable binder and a chemical ablation agent in a concentration effective to cause necrosis of said tissue, wherein said dosage form is a sterile, solid or semi-solid dosage form, and said biodisintegrable binder comprises first and second biodisintegrable polymers, wherein at least one of said first and second biodisintegrable polymers is crosslinked at an outer surface of the dosage form.

2. The dosage form of claim 1, wherein the dosage form is in the shape of a cylinder.

3. The dosage form of claim 1, wherein the dosage form is in the shape of a bead.

4. The dosage form of claim 1, wherein the dosage form is in the shape of a fiber.

5. The dosage form of claim 1, wherein the dosage form is a particulate dosage form having a weight average particle size between 1 and 100 microns in largest dimension.

6. The dosage form of claim 1, wherein the biodisintegrable binder comprises a glycolic acid polymer.

7. The dosage form of claim 1, wherein the dosage form is adapted for injection or insertion into the tissue via a jet injector.

8. The dosage form of claim 1, wherein the biodisintegrable binder comprises a biodisintegrable polymer.

9. The dosage form of claim 1, wherein the biodisintegrable binder comprises an organic compound.

10. The dosage form of claim 1, wherein the biodisintegrable binder comprises a cellulose ether.

11. The dosage form of claim 1, wherein the biodisintegrable binder comprises carboxymethyl cellulose.

12. The dosage form of claim 1, wherein the biodisintegrable binder comprises crosslinked alginic acid or a salt thereof 13. The dosage form of claim 1, wherein (a) said first biodisintegrable polymer is alginic acid or a salt thereof, and (b) said second biodisintegrable polymer is carboxymethyl cellulose.

14. The dosage form of claim 1, wherein said dosage form is encapsulated.

15. The dosage form of claim 1, wherein said dosage form is encapsulated in an encapsulant that comprises a biodisintegrable polymer.

16. The dosage form of claim 1, wherein said dosage form is encapsulated in an encapsulant that comprises a crosslinked biodisintegrable polymer.

17. The dosage form of claim 1, wherein said ablation agent of said dosage form is selected from a salt, an enzyme, an acid, an oxidizing agent, and a base.

18. The dosage form of claim 1, wherein said dosage form comprises from 1 to 95 wt % of said ablation agent.

19. The dosage form of claim 1, further comprising an imaging contrast agent.

20. The dosage form of claim 1, wherein said dosage form comprises from 5 to 80 wt % of said ablation agent.

21. The dosage form of claim 1, wherein said dosage form comprises from 1 to 80 wt % of said biodisintegrable binder.

22. The dosage form of claim 1, wherein said dosage form comprises from 5 to 50 wt % of said biodisintegrable binder.

23. An injectable or insertable dosage form for producing specific necrosis of tissue that comes into contact with the tissue comprising: a biodisintegrable binder and a chemical ablation agent in a concentration effective to cause necrosis of said tissue, wherein said dosage form is a sterile, solid or semi-solid dosage form and wherein the dosage form is a particulate dosage form having a weight average particle size between 1 and 100 microns in largest dimension and said biodisintegrable binder comprises first and second biodisintegrable polymers, wherein at least one of said first and second biodisintegrable polymers is crosslinked at an outer surface of the dosage form.

24. The dosage form of claim 1, wherein the largest dimension of the dosage form is between 1 mm and 30 mm.

* * * * *